United States Patent [19]
Butler et al.

[11] Patent Number: 5,499,063
[45] Date of Patent: Mar. 12, 1996

[54] MULTIFOCAL TRIAL FRAME SYSTEM

[75] Inventors: E. Dean Butler, Cincinnati, Ohio; Craig H. Risk, Tucson, Ariz.

[73] Assignee: Vision Express Group Limited, Nottingham, England

[21] Appl. No.: 232,735

[22] Filed: Apr. 25, 1994

[51] Int. Cl.⁶ ..................................................... G02C 7/06
[52] U.S. Cl. .................................. 351/54; 351/41; 351/55
[58] Field of Search ............................. 351/55, 54, 128, 351/41, 47, 57, 229

[56] References Cited

U.S. PATENT DOCUMENTS

| | | |
|---|---|---|
| 949,109 | 2/1910 | Blanchard . |
| 955,333 | 4/1910 | Hill . |
| 980,070 | 12/1910 | Cowan . |
| 1,002,580 | 9/1911 | Griffin . |
| 2,103,340 | 12/1937 | Schneck . |
| 2,835,161 | 4/1954 | Williams . |
| 2,842,029 | 7/1958 | Roth ............................. 351/55 |
| 4,289,386 | 9/1981 | Brandstetter ..................... 351/125 |
| 4,448,501 | 5/1984 | Cogez . |

Primary Examiner—William L. Sikes
Assistant Examiner—Hung Xuan Dang
Attorney, Agent, or Firm—Thompson, Hine And Flory

[57] ABSTRACT

A multifocal trial frame system includes a trial frame shaped to engage the head of a wearer and which includes an adjustable nose bridge and a pair of downwardly-depending studs which are laterally adjustable relative to the nose bridge, a pair of lens brackets adjustably attachable to the studs, each including first and second lens rims; a pair of distance prescription lenses shaped to be retained by the first pair of rims; and a pair of multifocal lenses shaped to be received by the second pair of rims. The multifocal lenses each include a neutral portion and an insert portion having a close-viewing prescription. The insert portion is incorporated into the neutral portion to form a continuous, unitary lens with the neutral portion, so that the distance and the multifocal lenses cooperate to simulate multifocal eyeglasses of a predetermined prescription and configuration. In a preferred embodiment, the trial frame system includes a plurality of pairs of distance prescription lenses, each of a different predetermined magnification, a plurality of multifocal lenses, each pair having an insert portion of a different, predetermined configuration and magnification. The trial frame system thus is able to simulate multifocal lenses of the executive, graduated, flat top, trifocal and above-and-below configurations, and for the first time, make it possible for a patient to make a subjective evaluation of the performance and merits of a multifocal lens design.

42 Claims, 4 Drawing Sheets

MULTIFOCAL TRIAL FRAME SYSTEM

BACKGROUND OF THE INVENTION

The present invention relates to trial frame devices for eyeglasses and, more particularly, to trial frame systems for simulating multifocal eyeglass prescriptions.

In the course of an eye examination, it is common for a prescriptioner to demonstrate a number of different lens powers and styles to the patient. This frequently is accomplished by the use of a trial frame, such as that disclosed in Cogez U.S. Pat. No. 4,448,501. Such a trial frame is capable of closely replicating the desired eyeglass prescription. However, the device disclosed in the aforementioned patent is only capable of simulating the prescription of single focus eyeglasses; it is not capable of simulating a multifocal eyeglass prescription.

Since a large number of the eyeglass-wearing public requires multifocal lens prescriptions, there is a need to provide a trial frame system which simulates a multifocal eyeglass prescription. Several attempts have been made to provide such a trial frame system, and are disclosed in Hill U.S. Pat. No. 955,333; Cowan U.S. Pat. No. 980,070; Griffin U.S. Pat. No. 1,002,580 and Williams U.S. Pat. No. 2,835, 161.

Today, there are large numbers of different multifocal eyeglass styles and lens shapes, including the graduated (no line), executive, flat top, trifocal, round, curve top and above-and-below styles. Of course, each of those styles may be prescribed in a variety of magnifications and sizes to address the growing need for lenses specifically suited to an occupation or activity. Accordingly, a disadvantage common to all of the aforementioned multifocal trial frame systems is that it is not possible to mount the more modern multifocal lens designs due to the lens mounting mechanisms employed, which only allow for stacking of single vision lenses. Further, none of the systems disclosed in the aforementioned patents are capable of accurately simulating the look and feel of a particular multifocal eyeglass prescription.

Accordingly, there is a need for a multifocal trial frame system which is sufficiently flexible to approximate a wide range of multifocal eyeglass prescriptions, and which is capable of providing the subject with a realistic look and feel of a particular multifocal eyeglass prescription.

SUMMARY OF THE INVENTION

The present invention is a multifocal trial frame system which is sufficiently flexible to simulate a wide variety of multifocal eyeglass prescriptions with a manageable number of lens units, and is designed to provide the subject wearer with a realistic look and feel of the actual multifocal prescription. The present invention, unlike prior art devices, utilizes multifocal lens designs commonly available in the marketplace.

The trial frame system of the present invention includes a trial frame with temples having padded ends shaped to fit a variety of head sizes, and a pair of downwardly depending bosses, each of which is independently laterally adjustable relative to the frame, and a vertically adjustable nose bridge. Each of the bosses receives a lens support bracket having a pair of rims. The first rim is position adjacent to the eye of the wearer and is shaped to receive a round distance prescription lens. The second rim is positioned adjacent to the first rim opposite the eye of the wearer and is shaped to receive a multifocal lens which is larger than the distance lens.

The multifocal lens includes a neutral portion and an insert portion having a close-viewing prescription. The insert portion is incorporated into the neutral portion to form a continuous, unitary lens unit with the neutral portion. The lens support bracket holds the distance and multifocal lens units in a substantially parallel relationship so that the lenses cooperate to simulate a specific multifocal eyeglass prescription.

In the preferred embodiment, there are a plurality of round, distance prescription lenses of varying dioptric powers. Similarly, there are a plurality of multifocal lens unit pairs, each simulating a particular multifocal lens prescription and multifocal lens style, so that when combined with the appropriate distance prescription lens, the combination is capable of simulating virtually all varieties of multifocal lens dioptric powers and styles.

Accordingly, it is an object of the present invention to provide a multifocal trial frame system which is capable of simulating a wide variety of multifocal lens prescriptions and styles with a manageable number of lens units; a multifocal trial frame system which is capable of simulating the look and feel of a wide variety of multifocal lens prescriptions; a multifocal trial frame system which utilizes a single trial frame which is sufficiently adjustable to fit comfortably a large range of head sizes; and a multifocal trial frame system which is relatively inexpensive to manufacture and adjust and is lightweight when worn.

Other objects and advantages of the present invention will be apparent from the following description, the accompanying drawings and the appended claims.

DETAILED DESCRIPTION

Figure 1:
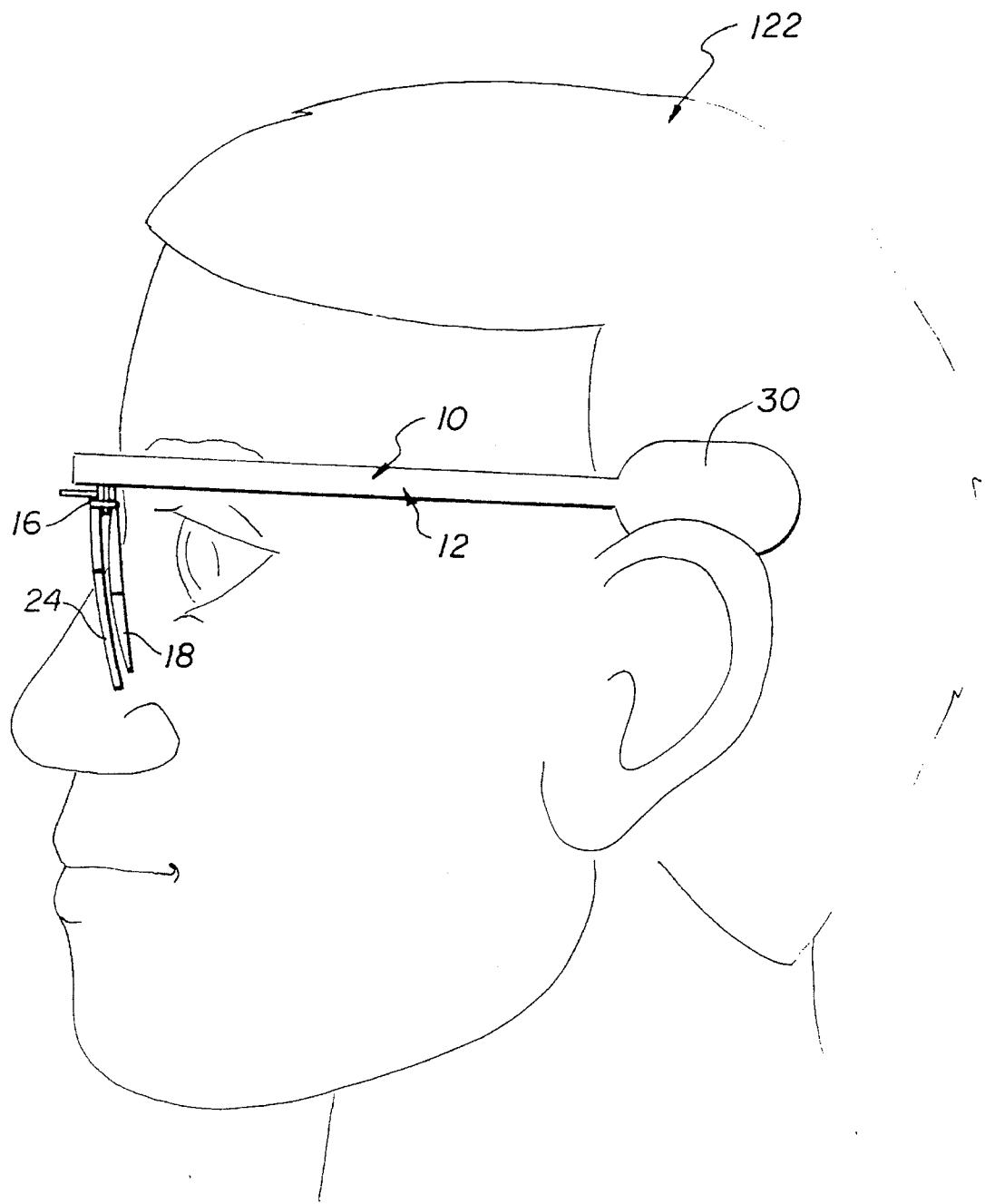
FIG. 1 is a side elevation of the preferred embodiment of the multifocal trial frame system of the present invention, shown worn by a subject.
Figure 2:
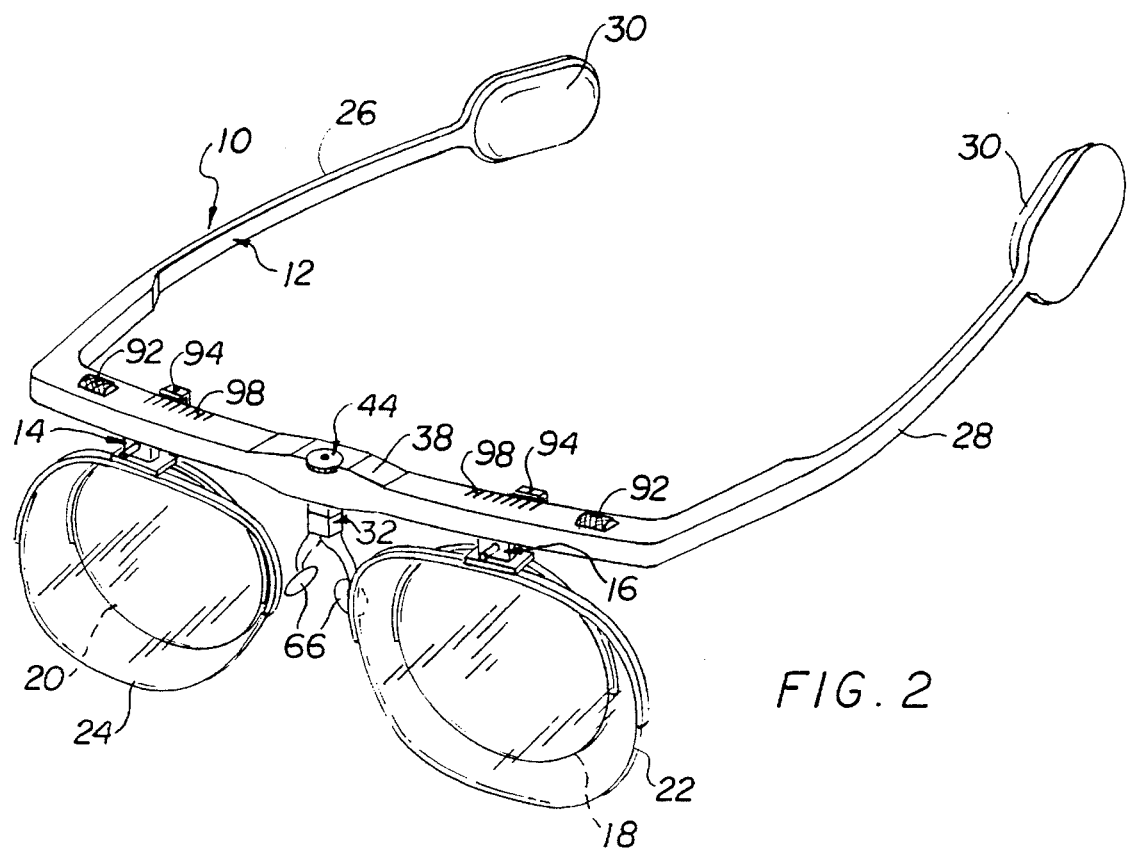
FIG. 2 is a perspective view of the trial frame system of FIG. 1.

As shown in FIGS. 1 and 2, the multifocal trial frame system of the present invention, generally designated 10, includes a trial frame 12 that supports a pair of lens brackets 14, 16, each of which supports a pair of distance prescription lens units 18, 20, and a pair of multifocal lens units 22, 24, which are of a type commonly available in the marketplace. The frame 12 includes a pair of flexible, resilient stems 26, 28, each terminating in an enlarged, resilient pad 30. The stems 26, 28 and pads 30 are sufficiently flexible so that the frame 12 is capable of fitting a wide variety of head sizes and shapes.

Figure 3:
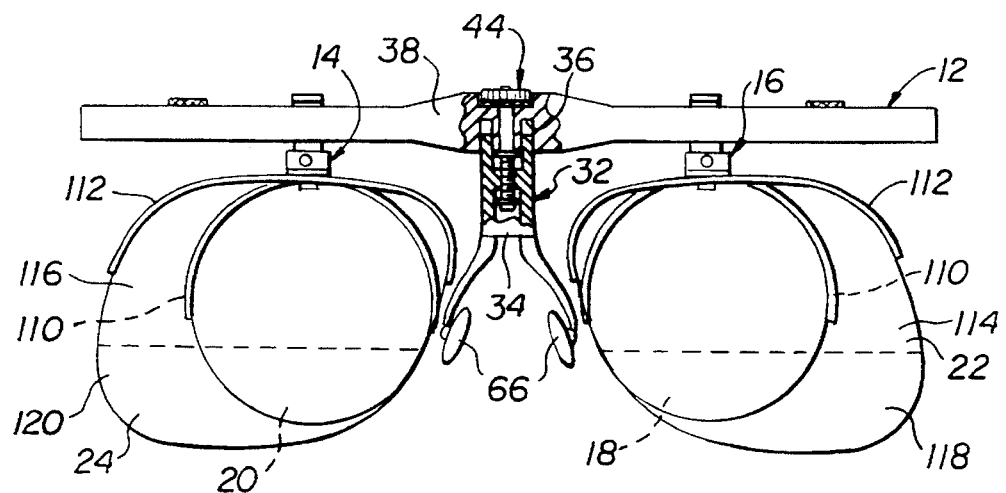
FIG. 3 is a front elevational view of the trial frame system of FIG. 1, in which the nose bridge assembly is partially broken away.
Figure 10:
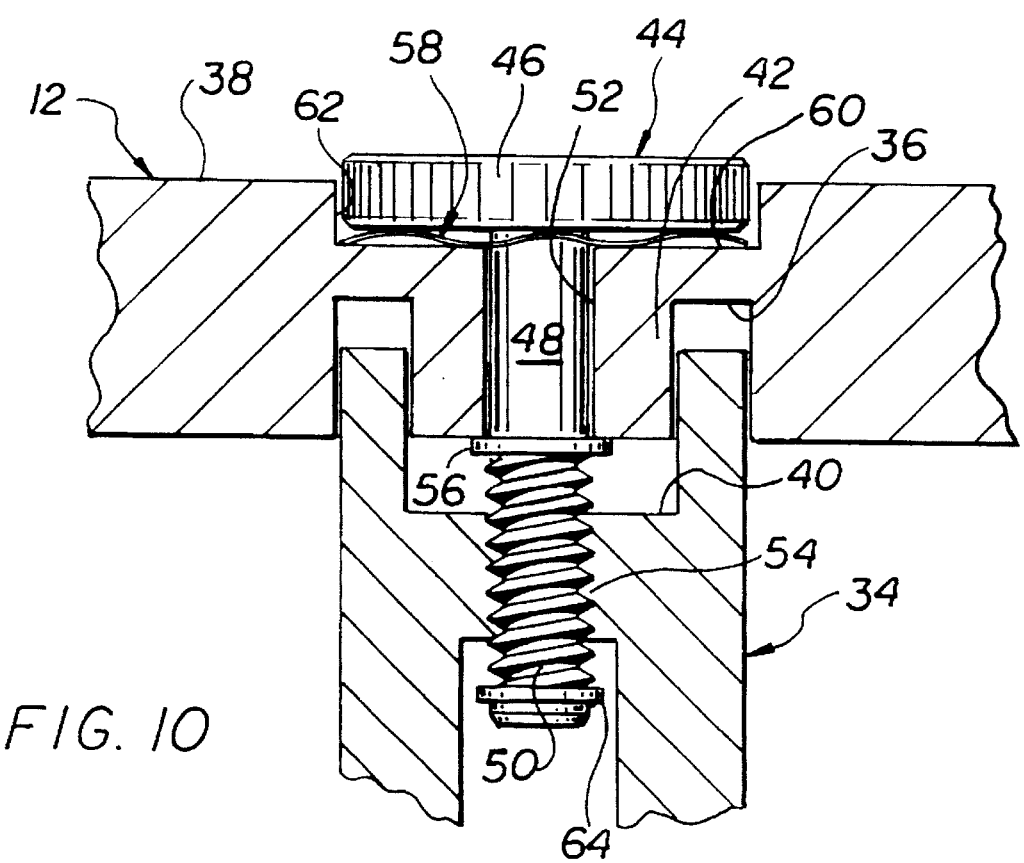
FIG. 10 is a detail of the nose bridge structure of the embodiment of FIG. 1.

As shown in FIGS. 2 and 3, the frame 12 includes a nose bridge assembly 32. Nose bridge assembly includes a stud 34 which is substantially rectangular in cross section and is shaped to be received within a correspondingly-shaped rectangular recess 36, set in the underside of the frame 12 at a central, thickened portion 38. As shown in FIG. 10, the stud 34 includes a recess 40 which is substantially rectangular in shape and is sized to receive a rectangular protrusion 42 formed in the recess 36. A thumb wheel 44 includes a disk 46 which protrudes slightly above the upper surface of the thickened portion 38, and a shaft 48 terminating in a threaded portion 50. The shaft 48 extends through a hole 52 formed in the thickened portion 38, and the threaded portion 50 engages a correspondingly threaded hole 54 formed centrally in the stud 34.

The thumb wheel 46 is retained within the thickened portion 38 by snap ring 56, and tension is applied to the snap ring by a spring washer 58 which is positioned between the thumb wheel disk 46 and the floor 60 of the recess 62 which receives the thumb wheel disk. A second snap ring 64 is retained on the threaded portion 50 to prevent the stud 34 from inadvertently being removed from the threaded portion. Consequently, rotation of the disk 46 causes the threaded portion 50 to rotate relative to the stud 34, which operates to displace the stud into or out of the recess 36. The stud 34 thus is vertically adjustable relative to the trial frame 12.

As shown in FIGS. 2 and 3, the stud 32 terminates in a pair of flexible, resilient arms terminating in nose pads 66 which are spaced to engage a variety of nose shapes comfortably.

Figure 4:
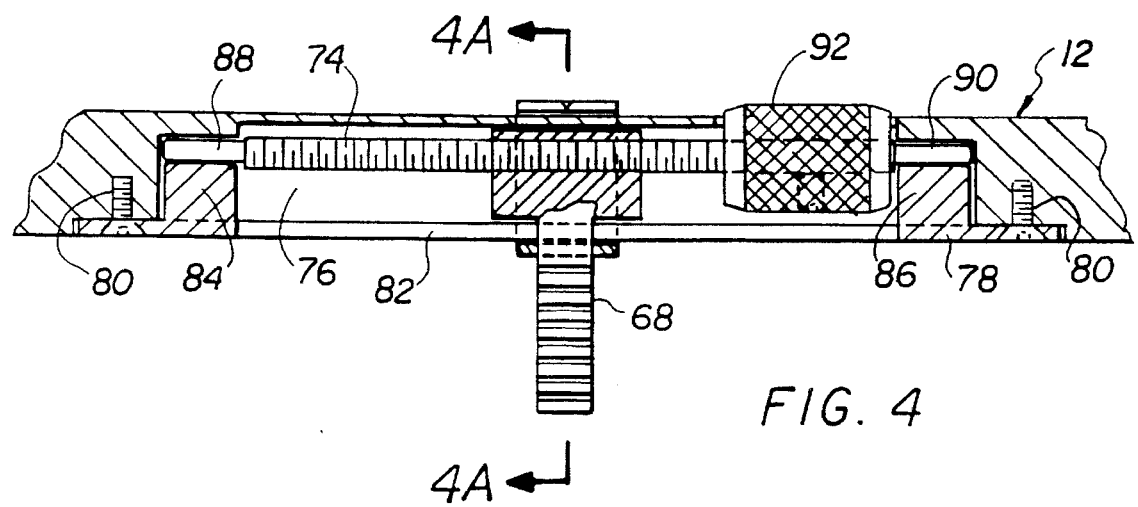
FIG. 4 is a detail of the adjustable boss structure of the system of FIG. 1.
Figure 4A:
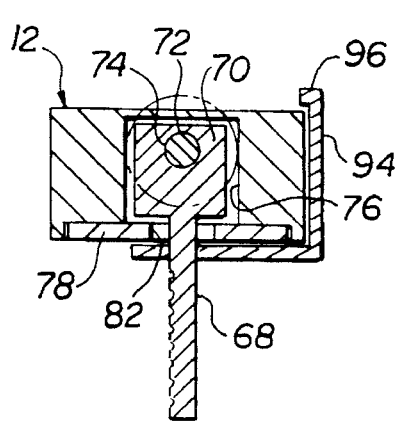
FIG. 4A is a sectional view taken at line 4A—4A of FIG. 4.

As shown in FIGS. 4 and 4A, the frame 12 includes a pair of downwardly depending bosses 68 (only the left boss is shown, it being understood that the structure of the right boss is identical thereto but of reverse hand). The boss 68 includes a rectangular nut 70 having a threaded hole 72 which receives a threaded rod 74 therethrough. The rectangular nut 70 and rod 74 are located within a rectangular slot 76 formed in the frame 12.

A retainer plate 78 is attached to the underside of the frame 12 by screws 80 and includes a slot 82 through which the stud 68 extends. The plate 78 includes bosses 84, 86 which are shaped to engage the ends 88, 90 of the threaded rods 74 and form journal bearings. A knurled wheel 92 is mounted on the threaded shaft 74 and protrudes above the upper surface of the trial frame 12 (see also FIG. 2).

An indicator arm 94, being generally L-shaped, is attached to the stud 68 and extends rearwardly and upwardly around the frame 12 to terminate in an indicator 96. The indicator 96 is positioned adjacent to graduated markings 98 inscribed on the upper surface of the frame 12 which indicate the horizontal pupillary distance from the stud 68 (and hence lenses 18, 22) to the center of the nose bridge 32. Accordingly, by rotating thumb wheel 92, the studs 68 can be displaced laterally relative to the frame 12 to adjust the horizontal pupillary distances between the lens pairs 18, 20, 22, 24.

Figure 9:
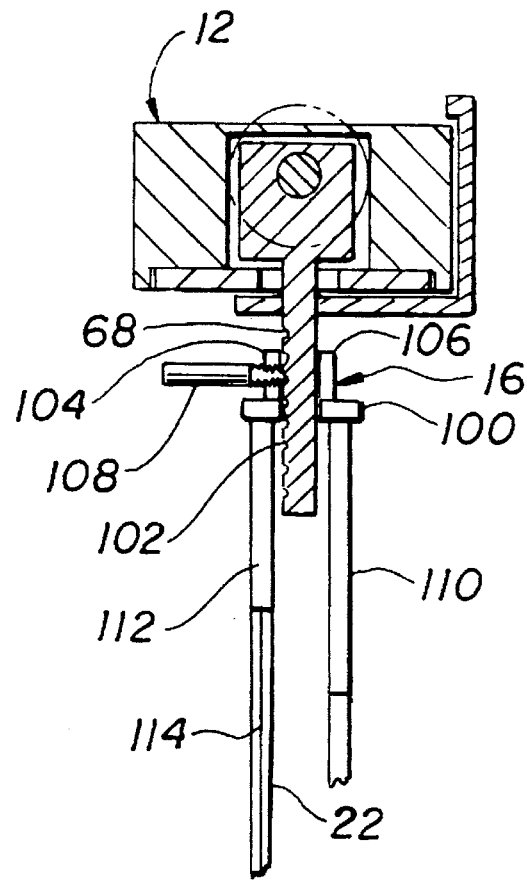
FIG. 9 is a detail elevation view in section of the lens support bracket of the embodiment of FIG. 1.

As shown in greater detail in FIG. 9, each of the lens brackets 14, 16 (only lens bracket 16 being shown) includes a plate 100 having an opening 102 shaped to receive the boss 68 therethrough. A pair of vertical flanges 104, 106 extend upwardly from the plate 100 and are spaced apart a distance sufficient to allow the boss 68 to be inserted therebetween. A set screw 108 is threaded into flange 104 and urges the boss 68 against flange 106 and plate 100. Accordingly, the plates 100, 104, 106 provide vertically adjustable engagement with respect to the boss 68.

An arcuate rim 110 is attached to and extends downwardly from the plate 100 and a second arcuate rim 112 extends downwardly from the plate 100 and is oriented substantially parallel to rim 110. Rim 110 is shaped to receive the circular, distance prescription lens 18 (see FIGS. 2 and 3) in a releasable engagement to facilitate easy substitution of lenses 18, 20 of varying dioptric powers. The rim 112 is shaped to receive the larger, multifocal lenses 22, 24, which are permanently attached by conventional means such as nylon thread 114. As shown in FIG. 9, the boss 68 is angled with respect to the frame 12 a sufficient amount to provide a 5° pantoscopic angle between the lenses 18–24 and the vertical. Further, the trial frame is positioned on the wearer to provide a distance of approximately 14 mm between the wearer's eye and the lenses 18, 20.

As shown in FIG. 3, the multifocal lenses 22, 24 each include a neutral portion 114, 116, and a multifocal insert portion 118, 120 having a close viewing power. In the case of lens units 22, 24 shown in FIG. 3, the multifocal style is the graduated or "no line" style. The multifocal portions 118, 120 are unitary with the neutral portions 114, 116 so that continuous lens units 22, 24 are formed.

Figure 5:
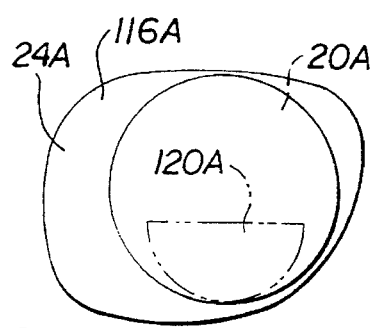
FIG. 5 shows a combination of distance and close viewing lenses with a flat top insert.

As shown in FIG. 5, multifocal lens unit 24A includes a neutral portion 116A and a multifocal insert portion 120A, having a close-viewing prescription. The insert portion 120A is a flat top multifocal lens (also known as straight top or "D" style).

Figure 6:
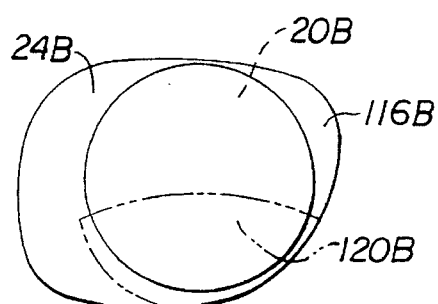
FIG. 6 shows the combination of FIG. 5, but with a different style flat top.

As shown in FIG. 6, multifocal lens unit 24B includes a neutral portion 116B and an insert portion 120B, which has a different curved top shape.

Figure 7:
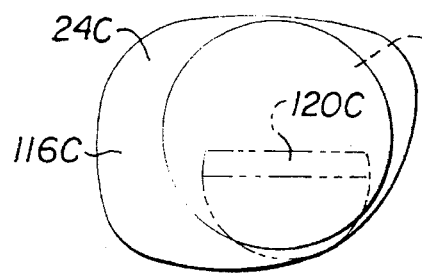
FIG. 7 shows the combination of FIG. 5, but with a trifocal insert.
Figure 8:
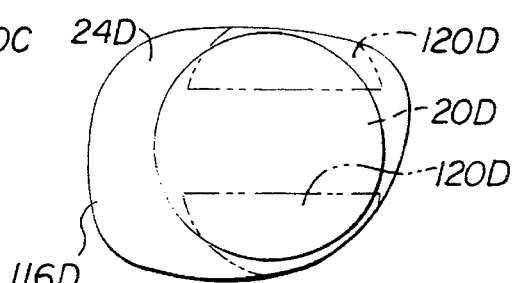
FIG. 8 shows the combination of FIG. 5, but with an above-and-below insert.

In FIG. 7, the lens unit 24C includes a neutral portion 116C and an insert portion 120C which is an occupational trifocal, flat top style. In FIG. 8, the lens unit 24D includes a neutral portion 116D and insert portions 120D which provide an above-and-below multifocal style (also known as double "D"s or double flat top style).

The method of using the trial frame system 10 is as follows. Having obtained a prescription from a doctor which specifies the correction for distance and near-point addition, the predetermined distance prescription is selected for the patient by selecting lenses 18, 20 of appropriate power. Next, the appropriate specification for the multifocal lens unit is made. This is determined, in part, by the subjective lifestyle requirements of the patient, as well as by the patient's occupational and recreational needs. The two sets of lens units are then placed in parallel relation on the lens brackets 14, 16 and attached to the trial frame 12.

The trial frame 12 is then adjusted so that the geometric centers of the lenses 18, 20 match the pupillary distance, when the far point fixation is parallel (the patient is looking at infinity). The vertical orientation of the lenses 18–24 is made by adjustment of the nose bridge 32 and position of the brackets 14, 16 on bosses 68, in order to determine the optimal vertical positioning of the multifocal segments 120.

The patient is now able to perform normal tasks, such as walking, reading, using a computer and negotiating stairs, and will receive a realistic idea of the effect of the lens design under those real life circumstances. For the first time, the patient will be able to make a subjective evaluation of the lens design before purchase.

Thus, as shown in FIGS. 3 and 5–8, a variety of multifocal lens styles can be created, each with a corresponding distance lens unit 20, 20A–20D of different prescriptions. In the preferred embodiment, the distance lens 20 is round and has a diameter of approximately 38 mm. The shape of multifocal lens unit 24 is preferably of the "aviator" style, having a height of approximately 42 mm and a width of approximately 54 mm. The lenses are oriented on their respective lens brackets 14, 16 (see FIGS. 2 and 3), such that the geometric centers of the multifocal lenses 22, 24 are offset from the geometric centers of the distance lenses 18, 20 so that the geometric centers of the distance lens units are 4 mm inward and 1 mm upward relative to the geometric centers of their adjacent multifocal lens units.

Since the distance lens units 18, 20 are removable from their respective rims 110, it is possible to combine a given multifocal lens 22, 24 with an entire range of distance prescription lens units 18, 20. This increases the flexibility of the system and minimizes the number of separate components required to provide a wide range of prescriptions and styles.

As shown in FIGS. 1 and 2, the trial frame system 10 closely approximates a conventional pair of eyeglasses in size and shape. Accordingly, it is possible for the wearer 122 (see FIG. 1) to wear the trial frame 12, walk about, read and perform normal tasks to determine the effect of the particular multifocal style (that is, the shape of the insert portions 118, 120) on his or her ability to see a transition from distance viewing to close viewing.

In the preferred embodiment, the frame 12 is made largely of plastic, and the boss assemblies and adjustable nose bridge are made of machined aluminum. However, it is within the scope of the invention to fabricate the trial frame system 10 of any suitable, light-weight material.

While the forms of apparatus herein described constitute preferred embodiments of the invention, it is understood that the invention is not limited to these precise forms of apparatus, and that changes may be made therein without departing from the scope of the invention.

What is claimed is:

1. A multifocal trial frame system comprising:

a trial frame shaped to engage the head of a wearer;

a pair of distance prescription lenses attached to said frame;

a pair of multifocal lenses attached to said frame and positioned adjacent to said distance lenses, each of said multifocal lenses including a neutral portion and an insert portion having a close-viewing power, said insert portion being incorporated into said neutral portion to form a continuous, unitary lens unit with said neutral portion, whereby said lenses cooperate to simulate multifocal eyeglasses of a predetermined prescription and configuration.

2. A multifocal trial frame system comprising:

means, shaped to engage the head of a wearer, for supporting lenses;

distance prescription lens means attached to said support means; and multifocal lens means attached to said support means and including a neutral portion and an insert portion having a close-viewing power, said insert portion being incorporated into said neutral portion to form a continuous, unitary lens with said neutral portion, whereby said lenses cooperate to simulate multifocal eyeglasses of a predetermined prescription and configuration.

3. The trial frame system of claim 2 wherein said multifocal lens means is shaped and positioned to overlie said distance prescription lens means substantially completely.

4. The trial frame system of claim 3 wherein said distance lens means is removable from said support means.

5. The trial frame system of claim 4 wherein said distance lens means comprises a plurality of pairs of distance lens units, each having a predetermined different prescription and being separately individually attachable to said support means.

6. The trial frame system of claim 5 wherein said multifocal lens means is removable from said support means.

7. The trial frame system of claim 6 wherein said multifocal lens means comprises a plurality of pairs of multifocal lens units, each having a predetermined different prescription and being separately individually attachable to said support means.

8. The trial frame system of claim 7 wherein said multifocal lens units include a pair of progressive lenses of a predetermined prescription.

9. The trial frame system of claim 7 wherein said multifocal lens units include a pair of trifocal lenses of a predetermined prescription.

10. The trial frame system of claim 7 wherein said multifocal lens units include a pair of above-and-below lenses of a predetermined prescription.

11. The trial frame system of claim 7 wherein said multifocal lens units include a pair of flat top lenses of a predetermined prescription.

12. The trial frame system of claim 2 wherein said support means includes trial frame.

13. The trial frame system of claim 12 wherein said trial frame includes boss means for attachment by said distance prescription lens means and said multifocal lens means, said boss means being laterally adjustable relative to said trial frame.

14. The trial frame system of claim 13 wherein said boss means includes a boss positioned to depend downwardly from said trial frame; and a thumbscrew rotatably mounted within said trial frame and engaging said boss.

15. The trial frame system of claim 14 wherein said boss means includes a pair of said bosses, each adapted to receive a different one of a pair of said distance lens means and said multifocal lens means.

16. The trial frame system of claim 14 further comprising lens bracket means for attaching said distance lens means and said multifocal lens means to said boss.

17. The trial frame system of claim 16 wherein said lens bracket means includes rim means for receiving said distance lens means and said multifocal lens means; rim means support plate, attached to said rim means and having an opening shaped to receive said boss therethrough; and means for clamping said boss to said support plate, whereby said lens bracket means is adjustably attachable to said boss and is displaceable relative to said trial frame.

18. The trial frame system of claim 17 wherein said clamping means includes a set screw threaded through said support plate and shaped to urge said boss against said support plate.

19. The trial frame system of claim 18 wherein said boss is oriented relative to said trial frame to provide a 5° pantoscopic angle.

20. The trial frame system of claim 19 wherein said rim means includes a first rim shaped to receive said distance lens means, said first rim being positioned adjacent to the eye of a wearer; and a second rim shaped to receive said multifocal lens means, said second rim being positioned on a side of said distance lens means opposite said eye of said wearer.

21. The trial frame system of claim 20 wherein said first and second rims are positioned relative to each other such that a geometric center of said distance lens means is decentered relative to a geometric center of said multifocal lens means inwardly and upwardly relative to said trial frame.

22. The trial frame system of claim 12 wherein said trial frame includes adjustable nose bridge means.

23. The trial frame system of claim 22 wherein said adjustable nose bridge means includes a recess formed in said trial frame; a stud shaped to be received within said recess; and thumb wheel means, rotatably attached to said trial frame and said stud, for displacing said stud into and out of said recess.

24. The trial frame system of claim 23 wherein said stud includes a pair of pads shaped to engage the nose of a wearer.

25. The trial frame system of claim 12 wherein said trial frame includes a pair of flexible, resilient stems shaped to urge against the head of a wearer such that a variety of head shapes can be accommodated.

26. The trial frame system of claim 25 wherein said stems each terminate in a resilient pad.

27. The trial frame system of claim 25 wherein said insert portion forms a continuous, unitary lens with said neutral portion, whereby said lenses cooperate to simulate multifocal eyeglasses of a predetermined prescription and configuration.

28. A multifocal trial frame system comprising:

means, shaped to engage the head of a wearer, for supporting lenses;

distance prescription lens means attached to said support means; and multifocal lens means attached to said support means and including a neutral portion and an insert portion having a close-viewing power, said neutral portion being shaped and positioned to overlie said distance prescription lens means substantially completely, said insert portion being incorporated into said neutral portion.

29. A method of simulating a look and feel of a multifocal lens prescription utilizing a trial frame system comprising the steps of:

selecting a trial frame shaped to engage the head of a subject;

selecting a pair of distance prescription lenses of predetermined power and attaching said lenses to said frame;

selecting a pair of multifocal lenses of a predetermined power and style and attaching them to said frame adjacent to said distance prescription lenses, each of said multifocal lenses including a neutral portion and an insert portion having a close-viewing prescription, said insert portion being incorporated into said neutral portion to form a continuous, unitary lens unit with said neutral portion, whereby said lenses cooperate to simulate multifocal eyeglasses of a predetermined prescription and configuration; and placing said trial frame with said lenses on the head of said patient.

30. A method of simulating a look and feel of a multifocal lens prescription utilizing a trial frame system comprising the steps of:

selecting means, shaped to engage the head of a patient, for supporting lenses;

selecting distance prescription lens means of a predetermined prescription and attaching said distance prescription lens means to said support means;

selecting multifocal lens means of a predetermined prescription and attaching said multifocal lens means to said support means, said multifocal lens means including a neutral portion and an insert portion having a close-viewing power, said insert portion being incorporated into said neutral portion to form a continuous, unitary lens with said neutral portion, whereby said lenses cooperate to simulate multifocal eyeglasses of a predetermined prescription and configuration; and placing said support means with said lenses on the head of said patient.

31. The method of claim 30 further comprising the steps of: removing said multifocal lens means from said trial frame; and attaching second multifocal lens means having an insert portion of a different design to said support means.

32. A multifocal trial frame system comprising:

a trial frame shaped to engage the head of a wearer;

a distance prescription lens unit attached to said trial frame;

a multifocal lens unit attached to said trial frame and including a neutral portion and an insert portion having a close-viewing power, said insert portion being incorporated into said neutral portion to form a continuous, unitary lens unit with said neutral portion, whereby said lenses cooperate to simulate multifocal eyeglasses of a predetermined prescription and configuration;

said trial frame including a boss depending downwardly therefrom for attachment by said distance prescription lens unit and said multifocal lens unit, said boss being laterally adjustable relative to said trial frame and including a thumbscrew rotatably mounted within said trial frame and engaging said boss;

a lens bracket for attaching said distance prescription lens unit and said multifocal lens unit to said boss, said lens bracket including a rim assembly for receiving said distance prescription lens unit and said multifocal lens unit, a rim assembly support plate, attached to said rim assembly and having an opening shaped to receive said boss therethrough, and a clamp for clamping said boss to said support plate, whereby said lens bracket is adjustably attachable to said boss and is displaceable relative to said trial frame;

said clamp including a set screw threaded through said support plate and shaped to urge said boss against said support plate, said boss being oriented relative to said trial frame to provide a 5° pantoscopic angle; and said rim assembly including first and second rims shaped to receive said prescription distance lens unit, said first rim being positioned adjacent to the eye of a wearer, and said second rim shaped to receive said multifocal lens unit, said second rim being positioned on a side of said prescription distance lens unit opposite said eye of said wearer, said first and second rims being positioned relative to each other such that a geometric center of said prescription distance lens unit is decentered relative to a geometric center of said multifocal lens unit inwardly and upwardly relative to said trial frame, such that said center of said distance lens means is approximately 4 mm inward and 1 mm upward relative to said geometric center of said multifocal lens unit.

33. A multifocal trial frame system comprising:

a trial frame shaped to engage the head of a wearer;

a plurality of pairs of distance prescription lenses, said pairs having different dioptric powers and being attachable to said frame;

a plurality of pairs of multifocal lenses, said pairs having different dioptric powers and being attachable to said frame adjacent to said distance prescription lenses, each of said multifocal lenses including a neutral portion and an insert portion having a close-viewing prescription, said insert portion being incorporated into said neutral portion to form a continuous, unitary lens unit with said neutral portion;

whereby said lenses cooperate such that a multiplicity of predetermined multifocal eyeglass prescriptions and configurations can be simulated.

34. The trial frame system of claim 33 wherein said multifocal lenses include a pair of progressive lenses of a predetermined prescription.

35. The trial frame system of claim 33 wherein said multifocal lenses include a pair of trifocal lenses of a predetermined prescription.

36. The trial frame system of claim 33 wherein said multifocal lenses include a pair of above-and-below lenses of a predetermined prescription.

37. The trial frame system of claim 33 wherein said multifocal lenses include a pair of flat top lenses of a predetermined prescription.

38. A multifocal trial frame system for simulating a plurality of multifocal lens styles comprising:

a trial frame shaped to engage the head of a wearer;

a pair of distance prescription lenses having a selected dioptric power and being attachable to said frame;

a plurality of pairs of multifocal lenses of a same, selected dioptric power, said pairs of multifocal lenses being attachable to said frame adjacent to said distance prescription lenses, said multifocal lenses including neutral portions and insert portions being of different shapes and said insert portions being incorporated into said neutral portions to form a plurality of continuous, unitary lens units with said neutral portions;

whereby said lenses cooperate such that a multiplicity of predetermined multifocal eyeglass styles can be simulated by attaching various ones of said plurality of pairs of multifocal lenses to said trial frame.

39. The trial frame system of claim 38 wherein said insert portions include a pair of progressive lenses of a predetermined prescription.

40. The trial frame system of claim 38 wherein said insert portions include a pair of trifocal lenses of a predetermined prescription.

41. The trial frame system of claim 38 wherein said insert portions include a pair of above-and-below lenses of a predetermined prescription.

42. The trial frame system of claim 38 wherein said insert portions include a pair of flat top lenses of a predetermined prescription.

* * * * *